(12) United States Patent
Maspero et al.

(10) Patent No.: US 7,731,756 B2
(45) Date of Patent: Jun. 8, 2010

(54) BIODEGRADABLE BIOCOMPATIBLE IMPLANT

(75) Inventors: Fabrizio Alessandro Maspero, Zuich (CH); Kurt Ruffieux, Schlieren (CH)

(73) Assignee: Degradable Solutions AG, Schlieren (CH)

( * ) Notice: Subject to any disclaimer, the term of this patent is extended or adjusted under 35 U.S.C. 154(b) by 1036 days.

(21) Appl. No.: 10/540,323

(22) PCT Filed: Dec. 23, 2003

(86) PCT No.: PCT/EP03/14771
§ 371 (c)(1), (2), (4) Date: Feb. 6, 2006

(87) PCT Pub. No.: WO2004/056405
PCT Pub. Date: Jul. 8, 2004

(65) Prior Publication Data
US 2006/0136071 A1 Jun. 22, 2006

(30) Foreign Application Priority Data
Dec. 23, 2002 (EP) .................................. 02406138

(51) Int. Cl.
*A61F 2/28* (2006.01)
*A61C 8/00* (2006.01)
(52) U.S. Cl. ............... 623/23.51; 623/16.11; 433/201.1
(58) Field of Classification Search ....... 623/1.11–1.16, 623/16.11, 23.51; 433/201.1
See application file for complete search history.

(56) References Cited

U.S. PATENT DOCUMENTS

| 3,918,968 A | 11/1975 | Kukla et al. |
|---|---|---|
| 4,429,691 A | 2/1984 | Niwa et al. |
| 4,610,692 A | 9/1986 | Eitenmuller et al. |
| 4,645,503 A | 2/1987 | Lin et al. |
| 5,338,772 A | 8/1994 | Bauer et al. |
| 5,366,507 A | 11/1994 | Sottosanti |
| 5,433,751 A | 7/1995 | Christel et al. |
| 5,552,454 A | 9/1996 | Kretschmann et al. |

(Continued)

FOREIGN PATENT DOCUMENTS

DE 3106445 A1 11/1982

(Continued)

OTHER PUBLICATIONS

H.H. Lu, "3-D Porous Polymer-Bioactive Glass Composite Promotes Collagen Synthesis and Mineralization of Human Osteoblast-like Cells," Sixth World Biomaterials Congress Transactions, 2000 Society for Biomaterials, p. 972.

(Continued)

*Primary Examiner*—Suzette J Gherbi
(74) *Attorney, Agent, or Firm*—Buchanan Ingersoll & Rooney PC

(57) ABSTRACT

There is described a biocompatible implant for the filling of a cavity in a living organism such as, for example, a bone defect or an extraction wound, comprising an open porous scaffold and/or a composite matrix comprising a plurality of inorganic or synthetic granules and a synthetic polymer matrix, and further comprising a biodegradable membrane which is interconnectibly sealed to a surface portion of the scaffold or composite matrix such, that the scaffold or composite matrix and the membrane form a single piece of matter. In one embodiment, the implant is biodegradable.

38 Claims, 3 Drawing Sheets

U.S. PATENT DOCUMENTS

| | | | |
|---|---|---|---|
| 5,626,861 A | 5/1997 | Laurencin et al. | |
| 5,648,097 A | 7/1997 | Nuwayser | |
| 5,741,329 A | 4/1998 | Agrawal et al. | |
| 5,866,155 A | 2/1999 | Laurencin et al. | |
| 6,051,750 A * | 4/2000 | Bell | 623/11.11 |
| 6,054,142 A * | 4/2000 | Li et al. | 424/426 |
| 6,132,214 A | 10/2000 | Suhonen et al. | |
| 6,203,574 B1 | 3/2001 | Kawamura | |
| 6,376,472 B1 * | 4/2002 | Myers et al. | 514/44 |
| 6,455,024 B1 | 9/2002 | Glajch et al. | |
| 6,582,470 B1 * | 6/2003 | Lee et al. | 623/23.55 |
| 6,680,103 B1 | 1/2004 | Sloat et al. | |
| 6,783,712 B2 * | 8/2004 | Slivka et al. | 264/51 |
| 6,869,445 B1 | 3/2005 | Johnson | |
| 7,122,057 B2 * | 10/2006 | Beam et al. | 623/23.51 |
| 7,156,880 B2 * | 1/2007 | Evans et al. | 623/23.51 |
| 2001/0014831 A1 | 8/2001 | Scarborough | |
| 2002/0016636 A1 | 2/2002 | Ricci et al. | |
| 2002/0114933 A1 | 8/2002 | Gould | |
| 2005/0209704 A1 | 9/2005 | Maspero et al. | |

FOREIGN PATENT DOCUMENTS

| | | | |
|---|---|---|---|
| DE | 3134728 A1 | | 3/1983 |
| JP | 6-135439 | | 5/1994 |
| WO | WO 93/24097 A | | 12/1993 |
| WO | WO 00/35510 | * | 6/2000 |
| WO | WO 00/35510 A | | 6/2000 |
| WO | WO 00/50104 A1 | | 8/2000 |

OTHER PUBLICATIONS

International Search Report issued Jun. 21, 2004 in corresponding PCT/EP03/14771.

* cited by examiner

BIODEGRADABLE BIOCOMPATIBLE IMPLANT

The present invention concerns a biodegradable biocompatible implant for the treatment of defects in a living organism such as bone defects or tooth extraction wounds.

INTRODUCTION AND BACKGROUND OF THE INVENTION

Bone defects can be treated by the implantation of an autograft, an allograft, or a xenograft in the healing site. However, these biological implants suffer of many drawbacks, among them, for example, shortage of donor tissue, bacterial and viral contamination, etc. Biocompatible synthetic implants may present a safe and effective alternative for many indications.

In dental treatment, for example, the extraction of a tooth leaves an open wound that might be contaminated by bacteria. Moreover, it is a known problem, that due to the absence of the tooth, alveolar bone spontaneously undergoes remodeling, leading to its atrophy. Such atrophy may then cause many complications for subsequent reconstruction. In order to prevent this process, it has been suggested to implant into the extraction site a biocompatible, biodegradable open porous implant, which is configured and dimensioned to fit inside the tooth extraction socket. Unfortunately, the process of bone tissue regeneration competes with faster-growing soft tissue and epithelial cells, which tend to fill the bone repair site before sufficient bone growth is induced even when a osteoconductive scaffold is present.

To overcome this problem it is known from the prior art to employ a barrier material which is applied over the implant to exclude competitive cells and to avoid the migration of microscopic materials. This process is known as guided bone regeneration and involves a surgical placement and insertion of a barrier membrane which prohibits the in-growth of soft tissue and epithelial cells. Usually, after the initial surgical procedure, a removal of the membrane is necessary in order to avoid later inflammation and infection. There are also known biodegradable membranes which obviate the need for a subsequent removal operation. Nevertheless, these membranes are difficult to handle and implant. The surgical process is time consuming, cumbersome to the patient and involves considerably high costs.

In order avoid the drawbacks of the known prior art treatments with surgically placed membranes in WO 00/35510 it is suggested to provide the osteogenic bone graft with a zone of impermeability to soft tissue. The osteogenic bone graft comprises a coherent mass of bone particles from porcine or bovine bone. The zone of impermeability is obtained by reducing the porosity of a portion of the surface of the bone osteogenic graft This is achieved, e.g., by heating a portion of the surface area of the coherent bone mass, by crosslinking a portion of the surface area of the coherent bone mass and/or by applying one or more biocompatible masses to a portion of the surface area of the coherent bone mass to provide a microporous layer thereon and by combinations of the processes. By this treatment the zone of impermeability is formed as an integral, indivisibly interconnected portion of the osteogenic bone graft so as to form a single, unified whole which distinguishes from bone grafts which are combined with a separate barrier membrane material.

While the osteogenic bone grafts of WO 00/35510 avoid the drawbacks of prior art bone grafts which may be or may not be combined with surgically placed barrier membranes they too suffer from drawbacks. The base material for the bone particles usually is a natural, organically obtained porcine or bovine bone with all naturally occurring inadequaties. The obtaining of the bone particles from bones of organisms necessitates careful purification steps in order to avoid organic and genetic impurities. The production process may also require demineralization procedures to ensure that the inorganic mineral content is reduced to the required extent to obtain the desired porosity. These procedures are time consuming, cumbersome and involve considerable apparative and laborious efforts. The resultant product, thus, is rather scarce and costly. Moreover, the bone grafts from bone particles degrade very slowly and are rather incorporated in the host bone tissue.

While the problems of the prior art have been described with reference to dental problems it will be appreciated by those skilled in the art that implants are also used as treatments for other skeleton parts. If, for example, a part of the skeleton is stricken by a tumor, the area stricken by the tumor may be removed and replaced by an implant. In that case with the implants known from the prior art similar problems as those described with respect to dental treatments may arise.

OBJECTS AND SUMMARY OF THE INVENTION

It is an object of the present invention to overcome the drawbacks of the prior art bone grafts and osteoconductive scaffolds. There is to be provided a biocompatible and optionally biodegradable implant for the treatment of defects in a living organism such as bone defects or extraction wounds which reliably prohibits an in-growth of faster growing soft tissue and epithelial cells into the implantation site. A surgical placement and later removal of barrier membranes shall be avoided. In one embodiment there is provided a biocompatible and optionally biodegradable implant having a controllable open interconnected macro porosity, which allows an in-growth of regenerating bone tissue. In another embodiment there is provided a biocompatible and optionally biodegradable implant comprising a composite matrix that includes inorganic particles or granules bound together by a solid or porous organic polymer matrix. In both embodiments there is further provided a membrane covering that provides a zone of impermeability to soft tissue and/or epithelial cell in-growth.

It is a further object of the present invention to provide a biodegradable biocompatible implant which may be assembled and shaped easily in the desired manner to a defect-analogous implant in order to avoid hollow spaces between the implant and the sidewalls of the cavity. The biodegradable biocompatible implant shall be made of reproductively obtainable base materials. In one embodiment, the base materials are of synthetic nature and allow an easy preparation of the biocompatible implant.

The biocompatible implants according to the invention are advantageously made of synthetic, biocompatible and biodegradable materials. In the present invention, the synthetic biocompatible and biodegradable materials are defined as any biocompatible and biodegradable materials, which are not derived from tissues of vertebrate animals.

In the present invention, the following biocompatible and biodegradable materials are considered as synthetic materials:

chittin and chitosan, which may be derived from tissues of marine non vertebrate animals, hyaluronic acid, a polysaccharide, which can be obtained from rooster comb or by microorganism fermentation.

poly(amino acids) and polypeptides, which may be produced by biotechnological processes.

any polysaccharide, which is obtained from plants, from non vertebrate animals or by biotechnological processes. As example for such polysaccharides, we can mention alginate.

According to one embodiment of the invention an implantable biocompatible implant for the filling of a cavity in a living organism such as, for example, a bone defect or an extraction wound, is suggested comprising an open porous scaffold which is made for example from synthetic, biocompatible and biodegradable granules, and further comprising a biodegradable biocompatible membrane which is sealed to a surface portion of the scaffold such, that the scaffold and the membrane form a single piece of matter. The term "open porous scaffold" refers to a structural matrix of granules that are bonded or otherwise joined together so as to define a granular region comprising solid or porous granules and an open porous region comprising spaces or discontinuities between adjacent granules of the granular region. The open porous region may be filled with air or gas, at least initially, or it may be at least partially filled with liquid, solid particles, gel, and the like.

The scaffold or composite matrix can be obtained by fusing together granular biomaterial. Granules from synthetic, biocompatible and biodegradable materials are known in the art. They are obtainable in relatively simple processes and may be formed in reproducible shapes, porosities and sizes in any desired quantity. Time consuming costly purification and demineralization processes are not necessary. The zone of impermeability is formed by a biodegradable membrane. Examples of such membranes include surgically applied barrier membranes. They have the required barrier function and biocompatibility. The membrane is placed adjacent to an exposed surface of the scaffold or composite matrix. Thus, the interconnected scaffold or composite matrix and membrane form a single piece of matter which may be handled like a scaffold or composite without the membrane. The shape of the membrane is ideally matched to the shape of the exposed surface of the scaffold or composite matrix. Thus, there is no need for an alignment of the membrane after the insertion of the scaffold or composite matrix into a cavity.

A surgical placement and later removal of the barrier membrane is not required. The biodegradable biocompatible implant according to the invention consists of the scaffold or composite matrix and of the barrier membrane. The two components are distinct from each other, but they are practically inseparably connected with each other. The biodegradable biocompatible implant may be simply inserted into a bone defect or an extraction wound. The membrane on top of the exposed surface of the scaffold or composite matrix provides a safe barrier against an in-growth of faster growing soft tissue and epithelial cells into the implantation site. The process steps for the production of the biodegradable biocompatible implant are relatively simple and may be accomplished by the skilled physician or his assistance on location. Furthermore, standard forms of the biodegradable biocompatible implant may be produced as cones, cubes, cylinders, etc. at the manufacturing site, which can then be adapted by the physician as necessary. These standard biodegradable biocompatible implants may contain a membrane covering at least one zone of the surface of the biodegradable and biocompatible implant. The manufacture process is easy and fast to accomplish, resulting in comparatively low costs, which is an additional benefit for the patient.

The biocompatible scaffold or composite matrix may be formed by fusing together granules made of a synthetic, biocompatible and biodegradable material, such as biopolymers, bioglasses, bioceramics, more preferably calcium sulfate, calcium phosphate such as, for example, monocalcium phosphate monohydrate, monocalcium phosphate anhydrous, dicalcium phosphate dihydrate, dicalcium phosphate anhydrous, tetracalcium phophate, calcium orthophosphate phosphate, calcium pyrophosphate, $\alpha$-tricalcium phosphate, $\beta$-tricalcium phosphate, apatite such as hydroxyapatite, or polymers such as, for example, poly($\alpha$-hydroxyesters), poly (ortho esters), poly(ether esters), polyanhydrides, poly(phosphazenes), poly(propylene fumarates), poly(ester amides), poly(ethylene fumarates), poly(amino acids), polysaccharides, polypeptides, poly(hydroxy butyrates), poly(hydroxy valerates), polyurethanes, poly(malic acid), polylactides, polyglycolides, polycaprolactones, poly(glycolide-co-trimethylene carbonates), polydioxanones, or co-polymers, terpolymers thereof or blends of those polymers, or a combination of biocompatible and biodegradable materials.

In an alternative embodiment of the invention the synthetic biocompatible, biodegradable granules may be porous or hollow instead of being solid granules. The use of hollow and/or porous granules reduces the amount of implanted material and allows a better in situ integration. In a further advantageous embodiment, the granules may comprise at least one opening in the wall enclosing the interior hollow space, which opening in the wall is larger than micropores in the wall, and being preferably of macroscopic size. By providing the hollow biocompatible and biodegradable granules with an opening in the granule wall, the possibility of a tissue in-growth into the scaffold or composite matrix of the biocompatible and biodegradable implant is enhanced. The hole with an opening in the granule wall may be produced from slurry consisting of the biocompatible material, water and an adhesive (Wintermantel et al. 1996). Droplets of the slurry are brought onto a heated plate. The water in the slurry droplet boils and evaporates instantaneously out of the droplets leaving an evaporation crater in the droplet wall. When the droplets are cooled off, hollow granules having an opening in the granule wall are formed.

Preferably, synthetic biocompatible, biodegradable granules are selected, which have an equivalent-diameter of about 100 µm to about 2000 µm, preferably 500 µm to 1000 µm. Granules of the selected equivalent diameters are easily handled and readily further processed. While the term equivalent diameter indicates that the synthetic biocompatible and biodegradable granules may be of irregular shape, it is of advantage when it is provided with a regular shape. Preferably it has a generally spherical shape. Due to its homogeneous structure the spherical shape of the granular material allows a better handling and an easier estimation of the required quantity of granular material in order to fill a known volume of a cavity.

In one embodiment, a major portion of the granules are advantageously coated with at least one biocompatible and biodegradable layer of a polymer preferably selected from the group consisting of poly($\alpha$-hydroxyesters), poly(ortho esters), poly(ether esters), polyanhydrides, poly(phosphazenes), poly(propylene fumarates), poly(ester amides), poly(ethylene fumarates), poly(amino acids), polysaccharides, polypeptides, poly(hydroxy butyrates), poly(hydroxy valerates), polyurethanes, poly(malic acid), polylactides, polyglycolides, polycaprolactones, poly(glycolide-co-trimethylene carbonates), polydioxanones, or copolymers, terpolymers thereof or blends of those polymers.

The biocompatible and biodegradable coating layer of the synthetic granules has a thickness of 1 µm to 300 µm, preferably about 5 µm to about 30 µm. The mechanical stability of an implant made of coated granules depends on the thickness and the homogeneity of the coating. By an insufficient coating thickness the granules cannot stick together in the required extent. On the other hand, large amounts of coating materials can lead to the decrease of the pH-value in the vicinity of the implant during its degradation. Therefore, the optimal thickness of the biocompatible coating is a result of a compromise between implant stability and the amount of material, which will degrade. The preferred coating thickness of the granules may also be expressed as a weight fraction of about 4% to about 20% coating materials of the total weight of the scaffold, which may be loaded with additives such as plasticizers or biologically active substances. The biocompatible coating is made of a biodegradable polymer. Thus, it is ensured, that after a specified and defined time period the coated granular material may degrade or be resorbed or dissolve within the cavity without any residues.

The synthetic biocompatible, biodegradable granules may be spray-coated, preferably in a fluid bed machine, or immersion-coated with the desired biocompatible polymer(s). Both methods lead to the biocompatible and biodegradable granules having the required properties. The spray coating process in a fluid bed machine is preferred though, because it allows the fabrication of a great number of practically identical polymer-coated biocompatible and biodegradable granules in a very fast and economic manner. The technique is well proven and allows an easy control of the thickness of the coating layer(s) and the fabrication of biocompatible and biodegradable granules having multiple coating layers, which are distinct from each other. The coating in fluidized bed machine results in a homogenous and continuous coating, which offers a barrier against bacterial contamination of the granules or of implants made therefrom. During the coating process the granules do not adhere to each other, thus avoiding the formation of undesirable aggregates which might lead to highly inhomogeneous size distributions and coating thickness. The coated granules retain their excellent free-flow properties, which is necessary for an eventual further processing. Due to the homogeneity of the coating only a low amount of coating material, in particular PLGA, is required for the further consolidation of an implant. Thus, the risks of inflammation or tissue necrosis due to a massive release of acidic products in the environment of an implant during its degradation are significantly reduced. An integration of additives such as plasticizers or biologically active substances into the coating film(s) may be well controlled by the coating in a fluid bed machine. Thus, each granule is loaded with the same amount of the biologically active substances. The thickness of the coating is well controlled in the process. Therefore, even the release of an integrated biologically active substance is predictable and well controlled.

The coating of the synthetic biocompatible, biodegradable granules may comprise one or more layers of varying average thickness. At least the outmost coating layer is made of a biodegradable material. This embodiment of the invention allows providing the biocompatible and biodegradable granules with several coatings for specific purposes. The outmost biodegradable coating may be selected in accordance with a certain desired delay in degradability. Thus, the coating layer underneath is only exposed after a certain desired time period has expired. This, for example, allows a retarded delivery of a bioactive substance. Thus, the synthetic biocompatible and biodegradable granules may be coated with different coatings, which each is biodegradable and displays a specific effect.

It may be advantageous in some cases to provide a biocompatible, biodegradable scaffold or composite matrix, which comprises in addition non-coated synthetic biocompatible granules. The coated and uncoated synthetic granules are thoroughly mixed such, that they are safely fused together by the preferred method of production and still have the required stability. By providing a mixture of coated and non-coated granules for the production of the biocompatible and biodegradable implants, the amount of coating materials, which must degrade, may be further reduced.

The scaffold or composite matrix of the biocompatible, biodegradable implant may consist of one type of synthetic biocompatible, biodegradable granules only. In a preferred embodiment of the invention, the biocompatible, biodegradable implant is made of two or more kinds of coated granules. The term "different" includes synthetic granules having different sizes. The coated granules are distinct from each other and may consist of different biocompatible materials and/or comprise polymer-coatings, which are distinct from each other. Thus, an implant may be "designed" not only as an ideal match for a bone cavity or an extraction wound but also in accordance with further specific requirements, such as, for example, stability, resorption kinetic and/or solubility of the implant.

The scaffold or composite matrix of the biocompatible implant may be made of coated granules having micropores with average diameters of about larger than 0 to about 10 µm. By the fusion of the coated granules, the microporosity remains and/or macropores between the granules are formed having average diameters of about more than 10 µm to about 2000 µM, preferably about 100 µm to about 500 µm. It should be understood that the macropores between the particles comprising the scaffold can simply be void spaces filled with air or gas. It is also within the scope of the invention to at least partially fill some or all of the void spaces with a liquid, gel or solid (e.g., a plurality of particles such as a fine powder). The liquid, gel or solid may include one or more biologically active agents. The liquid, gel or solid may rapidly dissolve in contact with physiological fluids, or any kind of fluid, so that additionally space voids are created. It is also within the scope of the invention to prepare an implant comprising a shaped composite that includes few, if any, macropores (e.g., by using sufficient polymer between the solid granules so as to fill some or all of the void spaces and create a solid matrix).

It is to be noted that only the uncoated synthetic biocompatible, biodegradable granules have microporosity. Once the granules are coated the microporosity is practically not recognizable any more from the outside. Granules made of bioceramics, which have been sintered very densely, do not have a considerable microporosity at all. The porosity of the granular material and/or the scaffold of the biodegradable implant provides an even larger surface area. In addition the pores may be filled, e.g., with an antibiotic substance, with growth factors and like biologically active substances. Thus, the biocompatible and biodegradable implant, when implanted into a cavity or extraction wound not only fills the cavity, but permits the controlled release of biologically active substances. For example, the substance within the pores may be selected such that bacterial growth and the like more are hindered, such that bone formation is accelerated or such that pain at the bone wound is reduced.

By special selection of the biocompatible and biodegradable materials for the synthetic granules and their coatings, the growth and the proliferation of osteoblast-like cells may be supported during the degradation of the implant, which is finally replaced by newly formed bone tissue. The implant may in certain cases also prevent the erosion of the bone tissue surrounding the bone defect to be healed.

The biodegradable membrane is preferably a polymer film, a polymer textile, a polymer fleece or a layer of interconnected fused polymer particles or a combination thereof and sealed to the scaffold, thus forming at least one layer of impermeability to soft tissue and epithelial cells. The thickness of the membrane is preferably about 10 μm to about 3000 μm, preferably about 50 μm to about 1000 μm. The thickness can be selected in accordance with the kind of biodegradable polymer, in order to ascertain, that the duration of the degradation and resorption of the polymer membrane matches the duration required for the regeneration of the bone tissue.

In an embodiment of the invention, the membrane is made of a synthetic, biocompatible and biodegradable polymer selected preferably from the group consisting of poly(α-hydroxyesters), poly(ortho esters), poly(ether esters), polyanhydrides, poly(phosphazenes), poly(propylene fumarates), poly(ester amides), poly(ethylene fumarates), poly(amino acids), polysaccharides, polypeptides, poly(hydroxy butyrates), poly(hydroxy valerates), polyurethanes, ply(malic acid), polylactides, polyglycolides, polycaprolactones, poly(glycolide-co-trimethylene carbonates), polydioxanones, or co-polymers, terpolymers thereof or blends of those polymers.

The membrane may be formed by fusing polymer particles together such as for example microspheres, pellets or granules, having a size smaller than about 500 μm, preferably having a size about 1 μm to 200 μm.

The fusing of polymer pellets for the creation of the membrane may lead to the formation of pores in the membrane with sizes in the range of 1 μm to 500 μm, preferably of 5 μm to 50 μm. The size of the pores depends on the size of the polymer particles. The size of the particles is so selected such that the membrane may be porous, allowing the transport of fluids, but forming a barrier against soft tissue and/or epithelial cells in growth into the implant. The porosity can enhance the vascularization of the implant and, thus, promote the healing of the implantation site In a further embodiment of the invention, the membrane has at least two layers, one layer having a barrier function against soft tissue and/or epithelial cells in-growth in the scaffold and the second layer, which is direct in contact with the surrounding living organism serving for a stabilization and anchorage of the soft tissue which tends to close the wound, e.g. the stabilization of the gingival flap in the case of a tooth extraction wound.

In an alternative embodiment of the biodegradable, biocompatible implant at least one layer of the membrane is non-porous. The non-porous layer of the membrane prohibits the transport of fluids and the migration of microscopic materials, such as, e.g., bacteria, through the membrane. Thus, precautionary antibiotic measures may be omitted.

In a further embodiment of the invention a biologically active substance is integrated into the synthetic granules and/or into a coating applied to the granules and/or into the membrane coating of the implant, and/or forming a coating layer on the granules and/or implant itself and/or within the macropores between the granules. Thus, a controlled delivery of the biologically active substance is enabled. The amount of the biologically active substance may easily be defined by controlling the coating process, for example. By integrating biologically active substance into a submerged coating layer or region, or into the granular material itself, a controlled retarded release of the biologically active substance may be accomplished. The biological active substance can be also encapsulated in biodegradable microspheres and added to the granules for the preparation of the scaffold or composite matrix and/or the membrane.

The biocompatible, biodegradable implant may be used for tissue engineering applications. Hence, cells may be grown on the said implant. In another embodiment of the invention, the biocompatible, biodegradable implant may be seeded with cells.

The invention also suggests an easy to accomplish method for the production of a biocompatible implant for the treatment of defects in a living organism such as bone defects or extraction wounds. The method comprises the fusing of synthetic, biocompatible and biodegradable granules through polymer linkage within a mold to form a scaffold or composite matrix. A biodegradable polymer film, a biodegradable fleece, a biodegradable textile, biodegradable polymer granules, or a combination thereof is added on top of the scaffold or composite matrix within a mold and, through polymer linkage, is sealed to the scaffold or composite matrix. A membrane is hence created on a part of the implant creating a at least one zone of impermeability against soft tissue and/or epithelial cells in-growth.

The linkage of the synthetic granules is accomplished by subjecting them for a time span of at least about 3 seconds, typically for about 15 seconds to about 180 seconds to a pressurized $CO_2$ atmosphere, at a pressure of about 20 bar to about 200 bar, preferably about 50 bar and at a temperature of about 10° C. to about 100° C., preferably about 20° C. to about 37° C. The linkage of the biodegradable polymer film, the biodegradable fleece, the biodegradable textile, the biodegradable fused polymer particles, or a combination thereof may be performed simultaneously with the linkage process of the scaffold, or it may be performed in a second, separate step. If a second linkage step is required, the biodegradable polymer film, the biodegradable fleece, the biodegradable textile, the biodegradable fused polymer particles, or a combination thereof are linked with each other and with the surface of the scaffold within the mold by subjecting the contents of the mold for a further time span of at least about 3 seconds, typically for about 15 seconds to about 180 seconds, to a pressurized $CO_2$ atmosphere at a pressure of about 20 bar to about 200 bar, and at a temperature of about 10° C. to about 100° C., more preferably about 20° C. to about 37° C.

The $CO_2$ atmosphere acts as a slight solvent with respect to the polymer-coated granules and to the polymer film or the polymer granules of the barrier membrane. It enhances the linkage of the granules of the scaffold and of the barrier membrane with each other ensures a linkage of the polymer barrier membrane with the surface of the scaffold. The produced biocompatible and biodegradable scaffolds preferably comprise macropores in between the fused together synthetic granules. The macropores may be interconnected and have average sizes from about 10 μm to about 2000 μm, preferably about 100 μm to about 500 μm. The macropores serve to enhance the in-growth of tissue into the scaffold and thus allow a faster regeneration of the healing site.

In an alternative production method the synthetic granules are fused to a scaffold together with the membrane in the form of a biodegradable polymer film, a biodegradable fleece, a biodegradable textile, biodegradable fused polymer particles, or a combination thereof within a mold by subjecting the materials for a time span of at least about 10 seconds, typically of about 30 seconds to about 5 minutes to a beat treatment at elevated temperatures of about 50° C. to about 220° C., preferably about 80° C. to about 85° C.

When additives, such as plasticizers, are integrated into the polymer coating of the granules of the scaffold or composite matrix and/or in the material of the membrane, the glass transition temperature of polymeric material can be reduced. Hence, the process temperature for the fusion of the scaffold or composite matrix and the membrane can be reduced as low as room temperature or even lower.

The porosity of the membrane may be reduced by subjecting the membrane to a final heat treatment, preferably by exposure to an infra-red lamp or the like, at a temperature of about 100° C. to about 220° C., preferably 120° C. to 140° C. for a time span of about 1 s to about 120 s, preferably about 20 s to 60 s. This additional heat treatment process allows to prepare a barrier membrane without any porosity.

A preferred field of use for the biocompatible, biodegradable implant according to the invention is the application as a temporary replacement for an extracted tooth root or the like. Fusing of the individual synthetic polymer-coated granules to a matching scaffold and the addition of a barrier membrane may be accomplished very easily and very fast on-site from prefabricated biocompatible and biodegradable particles.

The biocompatible implants are made from coated granules of a synthetic, biocompatible material. They may also comprise uncoated granules. The granules are preferably fused together in a mold having a cavity corresponding to the required shape. The barrier membrane is formed and linked with the scaffold of the biocompatible implant within the mold by a $CO_2$ process or by a heat treatment. After removal from the mold, the biocompatible implant needs not be finished but may be directly inserted into a bone cavity or an extraction wound. However, due to the relatively high stability of the implants, they may even be further finished, such as, for example, by cutting away portions of the implant, if the need arises.

The incorporation of biologically active substances, such as growth factors for example, into a biocompatible, biodegradable implant may also be achieved very easily by mixing loaded microspheres with the synthetic biocompatible coated granules and/or particles. This allows a manufacture of the coated granules and/or particles under non-aseptic conditions with subsequent sterilization, while the microspheres, which carry the growth factors, may be produced under aseptic conditions. The mixing of the coated granules and the microspheres is done just before the preparation the biocompatible implant. The bonding is preferably achieved in a gaseous $CO_2$ atmosphere at low temperatures of about 20° C. to about 37° C., and a pressure of about 20 bar to about 200 bar, preferably about 30 bar to about 40 bar. Under these conditions and at such low temperatures, the growth factors may be handled easily with only little danger of degradation or alteration.

The preparation of the implant may be also be accomplished by a thermal process. However, the process parameters, such as, e.g., the temperature, must be carefully selected in order to prevent any degradation or alteration of the biological active substances.

BRIEF DESCRIPTION OF THE DRAWINGS

Further advantages of the invention will become apparent from the description of exemplary embodiments of the invention with reference to the accompanying drawings in which.

DETAILED DESCRIPTION OF THE INVENTION

Figure 1:
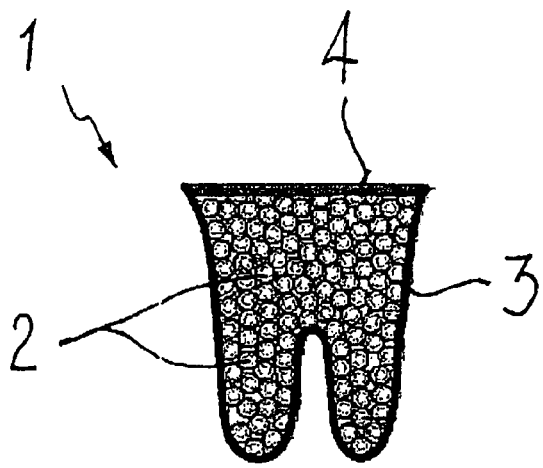
FIG. 1 is a schematic representation of a biocompatible implant according to the invention.

FIG. 1 is a schematic drawing of a biocompatible implant according to the invention. More specifically the representation shows a biocompatible and biodegradable implant 1 for implantation into a tooth extraction wound which is left by an extracted tooth in the alveolar bone. The biodegradable biocompatible implant 1 is shaped according to the root of the extracted tooth. It is produced from granules 2 of a synthetic, biocompatible and biodegradable material, such as, e.g., tricalcium phosphate (TCP). The granules 2 generally are of a regular, preferable spherical, shape. They may be solid or hollow with an opening in the granule wall. At least a portion of the granules 2 is provided with a coating of a biocompatible and biodegradable polymer. The coating is e.g. a polylactide and encloses the granules 2 completely like a shell. It has a thickness of about 1 µm to about 300 µm, preferably about 5 µm to about 20 µm. Coated and uncoated granules are fused together to form a scaffold 3 of interconnected granules. The interconnection is accomplished by polymer linkage of the polymer coating of neighbouring coated granules 2.

The upon implantation exposed upper surface of the scaffold 3 is covered with a barrier membrane 4 which is made of a biocompatible and biodegradable polymer, such as, e.g. polylactide. The barrier membrane 4 is interconnectibly sealed to the surface of the scaffold 3 such, that scaffold 3 and membrane 4 form a single piece of matter.

Figure 6:
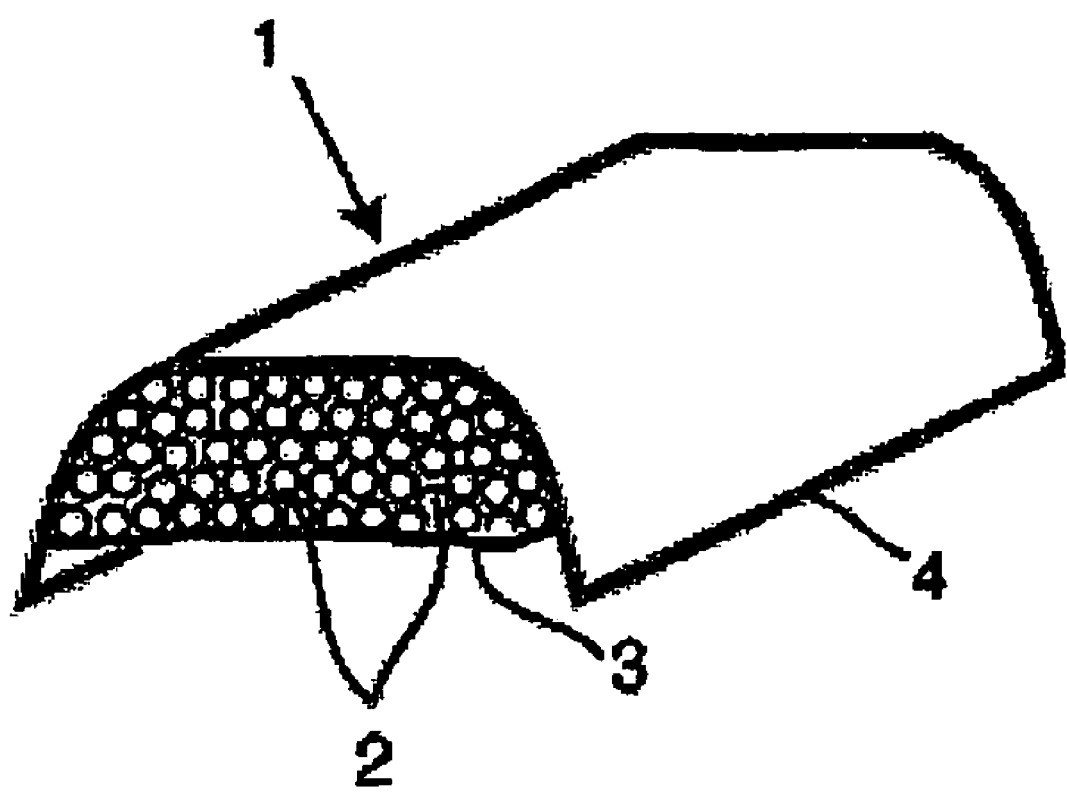
FIG. 6 is a schematic representation of a preformed biocompatible implant according to the invention, where the membrane exceeds the scaffold in size.

In FIG. 6, the representation shows a preformed biodegradable biocompatible implant 1 according to the invention, which is similar to the implant as described with reference to the exemplary embodiment depicted in FIG. 1. However, more than one exposed surface of the open porous scaffold 3, made of coated granules 2 is covered by a membrane 4. The membrane 4 exceeds the scaffold in size to prevent soft tissue and/or epithelial cell in-growth at the interface between bone and the biodegradable biocompatible implant.

Synthetic Base Material for Granules:

Preferred materials for manufacturing the granules include bioceramics such as calcium phosphates and calcium sulfates, bioglasses, and mixtures thereof. The calcium-based ceramics include, as monocalcium phosphate monohydrate (MCPM, $Ca(H_2PO_4)_2.H_2O$), monocalcium phosphate anhydrous (MCPA, $Ca(H_2PO_4)_2$), tetracalcium phosphate (TetCP, $Ca_3(PO_4)_2O$), calcium orthophosphate phosphate (OCP, $Ca_8H_2(PO_4)_6.5H_2O$), calcium pyrophosphate (CaP, $Ca_2P_2O_7$), dicalcium phosphate anhydrous (DCP, $CaHPO_4$), dicalcium phosphate dihydrate (DCPD, $Ca(H_2PO_4.2H_2O)$), β-tricalcium phosphate (β-TCP, $Ca_3(PO_4)_2$), α-tricalcium phosphate (α-TCP, $Ca_3(PO_4)_2$), and apatite such as hydroxyapatite (HA, $Ca_{10}(PO_4)_6(OH)_2$). Calcium phosphate ceramics are known for their excellent biocompatibility and are therefore used in various biomedical applications, HA and TCP among them being the most used bioceramics in orthopedic and maxillo-facial applications and for the treatment of bone defects. Their close ionic similarity with the mineral components of bone, their adjustable resorption kinetics to the need of a specific therapy and their bioactive properties have been mentioned before in the prior art. While HA is commonly considered to be non-biodegradable, some resorption behavior has been reported in in-vivo studies (Oonishi et al. 1999). β-TCP is generally considered to be biodegradable and is known to degrade faster than HA. After resorption of TCP in vivo new bone tissue is reported to replace the resorbed materials.

Preparation of β-TCP Granules:

From β-TCP powder granules are prepared, for example, by a spheronization route. 70 g β-TCP powder (purum p.a.>96%, Fluka, CH) is mixed with 1 g dextrin (Relatin Dextrin K51) in a mortar. 20 ml deionized water is slowly added to the powdery mixture under continuous stirring. The resultant paste is extruded through a multi-hole (ø: 800 μm) nozzle (Cyclo, Typ XYCG, Probst Technik, CH) and spheronized during ca. 3 min in a pelletrounder (Probst Technik, CH) in order to obtain granules having an average diameter of about 350 μm to about 1000 pin. The obtained β-TCP granules with a diameter between 500 and 1000 μm are then calcinated and sintered at a temperature of 1150° C. during 4 hours in a furnace (Nabertherm, CH).

Other method such as high-shear mixer and fluidized bed granulation can also be used in order to produce rounded granules.

Biocompatible and Biodegradable Polymer-coating of Granules:

Meanwhile a large number of biocompatible and biodegradable polymers are known from the prior art, among poly (α-hydroxyesters), poly(ortho esters), poly(ether esters), polyanhydrides, poly(phosphazenes), poly(propylene fumarates), poly(ester amides), poly(ethylene fumarates), poly (amino acids), polysaccharides, polypeptides, polyurethanes, poly(malic acid), polylactides, polyglycolides, polycaprolactones, poly(glycolide-co-trimethylene carbonates), polydioxanones, or co-polymers, terpolymers thereof or blends of those polymers. By way of example only the invention will be illustrated with reference to poly-lactide-co-glycolide (PLGA), which is known for its biocompatibility and biodegradability. For this purpose, a solution of PLGA in dichloromethan ($CH_2Cl_2$) is first prepared. The concentration of the polymer was about 0.1 g to 0.2 g PLGA in 1 ml $CH_2Cl_2$. The β-TCP granules are immersed in the PLGA solution. While the resultant mixture is constantly stirred, the solvent evaporates until a thin film of polymer is deposed on the surface of the β-TCP granules. Agglomerated granules can be then separated using a labor mixer and sieved. The extraction of the solvent is finally carried out for 36 h under vacuum (100 mbar).

A far more economic coating method, which results in a very homogenous coating of the β-TCP granules is the spray coating process in a fluidized bed machine. This coating process is well known from the prior art and has proven to achieve the desired homogenous coating results.

It is apparent to those skilled in the art that by selecting different coating solutions and varying the coating time, different layers of coatings having different thicknesses may be applied to the β-TCP granules. This includes the coating with biologically active substances as an individual coating or mixed or dissolved in the polymer coating.

Preparation of Scaffolds or Composites Matrix for Biocompatible and Biodegradable Implants:

β-TCP-PLGA biodegradable biocompatible implants are prepared from β-TCP granules, which are coated with at least one layer of PLGA. Various methods for the fabrication of implants may be used in order to fuse the polymer-coated granules together, among them heat treatments, application of solvents, use of pressurized $CO_2$, chemical linkage, mechanical fusion by applying pressure, and mixtures of those methods.

Process A

By a fusion method, which applies a heat treatment at elevate temperatures the scaffold of the biocompatible and biodegradable implant may be prepared as follows:

700 mg PLGA coated β-TCP granules are poured into a polysiloxane mold, having the desired shape, and heated to a temperature of about 80° C. to about 100° C. The granules are slightly compressed in the mold and kept at 80° C. to about 100° C. for at least about 5 seconds. Typically the process time amounts to about 10 seconds to about 5 minutes, preferably for about 1 minute to about 3 minutes.

Process B

The fusing of coated granules applying a method using pressurized $CO_2$ may be carried out as follows:

After filling a polysiloxane mold with a desired shape with 700 mg PLGA coated F TCP granules, the mold is place in a high pressure vessel at room temperature. After clo sure of the vessel, $CO_2$ is introduced into the vessel until a pressure of about 50 bar is reached. The pressure is increased at a ramp of about 2 bar per second. Once the maximum pressure is reached, it is held for at least about 3 seconds. Typically the pressure is held for about 3 seconds to about 180 seconds, preferably less than 30 seconds. Then, the $CO_2$ pressure is decreased at a rate of about 0.5 bar per second until it equilibrates with the outer atmospheric pressure. The whole process is preferably performed at room temperature or at slightly elevated temperatures of about 24° C. to about 37° C. Such an implant has a porosity of ca. 55% and a median pore diameter of ca. 280 μm.

Since the β-TCP granules are homogeneously coated with PLGA they are capable of fusing together during the $CO_2$ treatment. The $CO_2$ acts as a solvent for the coating. This results in a decrease of the glass transition temperature ($T_g$) of the polymer below the processing temperature. By the combination of the gas pressure and the reduction of $T_g$ the granules are able to fuse by polymer linkage only. Thus, it is apparent that a homogenous coating of the granular base material is an essential prerequisite for the fusing of the coated granules. The implants comprise interstitial spaces in between the fused granules. The size of the interstitial spaces is depending on the thickness of the coating, on the compaction of the implant, and on the size of the coated granules. Thus, an application of moderate additional pressure on the mold cavity during the fusing of the granules reduces the interstitial space and allows a control thereof. A scaffold having larger interstitial spaces may be desirable in order to provide room for the in-growth of newly formed tissue.

Preparation of Scaffolds or Composite Matrices of Biocompatible and Biodegradable Implants Loaded with Biologically Active Substances:

Process B using pressurized $CO_2$ for the fusing of the synthetic granules is preferred, because it permits to produce biocompatible and biodegradable scaffolds or composite matrices including, for example, PLGA microspheres loaded with biologically active substances such as insulin like growth factor-1 (IGF-1).

The preparation of biocompatible and biodegradable implants loaded with IGF-1 may be carried out as follows:

25 mg PLGA microspheres loaded with IGF-1 were mixed in a polysiloxane mould with 950 mg of coated granules using a small spatula. The granules used for this experiment were coated with PLGA in order to achieve a material compatible interface between the granules and the microspheres. For a homogenous microsphere distribution through the scaffold or composite matrix, the polysiloxane mould filled with the biomaterials was vibrated with a vortex device (level 3, Vortex Genie 2, Bender & Hobein, CH) during 20 s. In order to prevent the segregation of the microspheres on the bottom of the mould, the mould was turned upside down and the vibrating was repeated. The consolidation of the scaffold or composite matrix was then achieved under pressurized $CO_2$ atmosphere at 30 bar during 60 s.

Preparation of the Barrier Membrane and Sealing to the Exposed Surface of the Scaffold or Composite Matrix:

The barrier membrane may be made of a polymer film, a polymer fleece, a polymer textile, a layer of fused polymer particles or a combination thereof.

EXAMPLE 1

For the preparation of a polymer film, PLGA may be used. The polymer powder is first compressed between two plates with a load of 100 kN at 140° C. during 10 min. With this process a polymer film having a thickness of about 200 μm is obtained. The film is cut into small pieces of about 10 mm×10 mm.

Figures 2A, 2B:
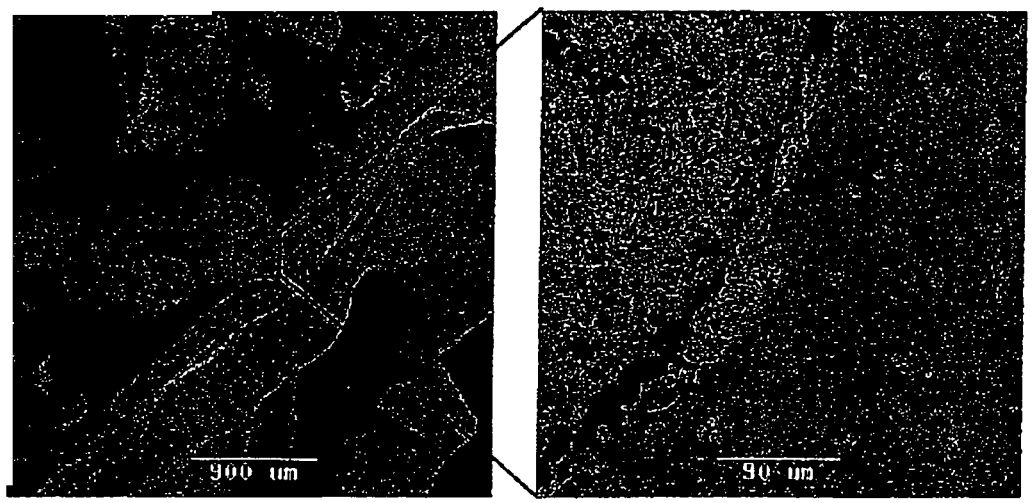
FIGS. 2a and 2b are electron microscope cross sectional views of a biocompatible implant with a non-porous membrane.

A scaffold or composite matrix is prepared in accordance with process A. Briefly, a mold is filled with β-TCP granules which are coated with PLGA. During the heat treatment the granules are gently compressed within the mold. After about 1 In to 3 min a piece of the polymer film is placed on the exposed surface of the scaffold or composite matrix. Because of the elevated temperature of the scaffold or composite matrix the film is malleable and may be easily manipulated in order to cover the entire surface of the scaffold or composite matrix. The polymer film links with the polymer coating of the coated granules of the scaffold or composite matrix. After cooling of the mold, the implant may be removed out of the mold. The implant is provided with a barrier membrane having a non-porous surface. This is shown in the cross sectional views in FIGS. 2a and 2b in which the large granules belong to the scaffold or composite matrix and the smooth film represents the non-porous barrier membrane. Even in the larger magnification in FIG. 2b no pores are visible on the surface of the membrane.

EXAMPLE 2

Polymer ganules are prepared from PLGA powder. The powder is compressed between two plates with a pressure of 100 kg/m² at 130° C. for about 40 min. After cooling a solid plate having a thickness of about 500 μm is obtained. The solid plate is cut into pieces which are ground in a centrifugal mill. After milling polymer granules with a size of about 100 μm to about 200 μm are obtained.

Figure 3:
FIG. 3 is an electron microscope cross sectional view of a non porous membrane formed from fused polymer particles.

A scaffold or composite matrix is prepared in accordance with the process in Example 1. The mold is then placed under an infra-red lamp which allows to heat the surface part of the polymer barrier membrane at about 130° C. After about 30 s of heat treatment the mold and the implant are allowed to cool. The implant is removed out from the mold. The implant is provided with a non-porous barrier membrane as is depicted in the electron microscope cross sectional view in FIG. 3.

EXAMPLE 3

Figure 4A:
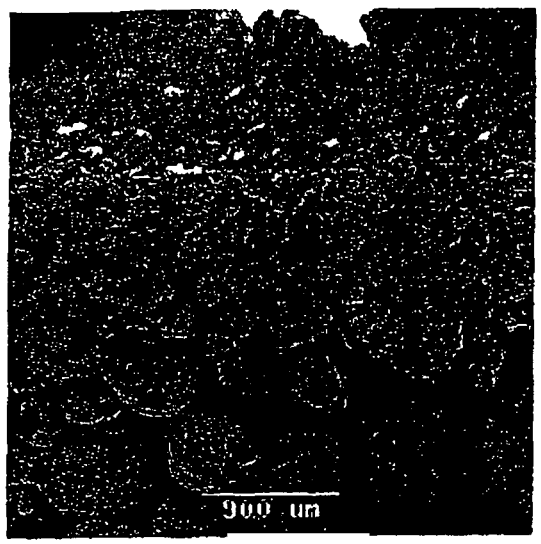
FIG. 4a is an electron microscope cross sectional view of a biocompatible implant with a macro-porous membrane.
Figure 4B:
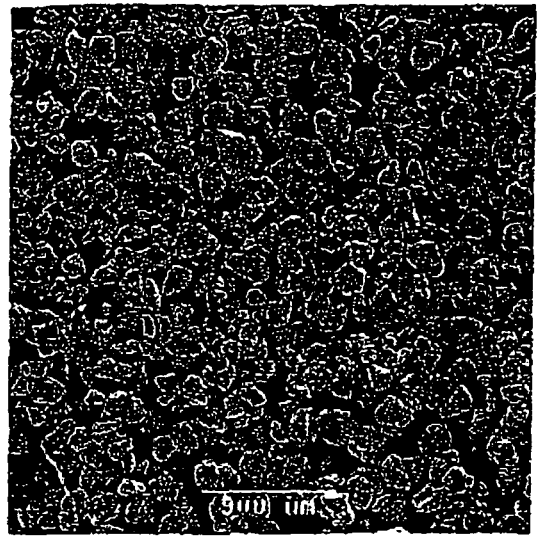
FIG. 4b is an electron microscope top plan view of the macro porous membrane.

The scaffold or composite matrix and the polymer particles are prepared as in Example 2. About 50 mg to 100 mg of polymer particles are poured into the mold on the exposed surface of the scaffold or composite matrix. After about 1 min to about 3 min at 80° C. to 100° C. the polymer granules have linked with each other and with the surface of the scaffold or composite matrix. The mold is allowed to cool and the biodegradable biocompatible implant is removed. With this process a biodegradable biocompatible implant is achieved having a barrier membrane sealed to its surface which is, in a preferred embodiment, macro-porous. The pores in this embodiment have sizes within a range of about 100 μm to about 500 μm. This is clearly shown in the cross sectional view in FIG. 4a, in which the large granules form a part of the scaffold while the smaller particles are a part of the barrier membrane. The top plan view of FIG. 4b shows the porosity of the exposed surface of the barrier membrane.

EXAMPLE 4

Polymer microspheres are prepared from PLGA. The microspheres are prepared using an emulsion/solvent extraction method. For that purpose first a polymer solution in ethyl acetate (6.25% w/w) is prepared. The solution is introduced dropwise into stirred PVA solution (0.4% w/w) such that an emulsion is formed. The emulsion is poured into 800 ml of water and stirred during about 5 h. The resulting solution is filtered. The obtained microspheres are dried under vacuum for about 12 h. The resulting microspheres have a size in the range from about 40 μm to about 100 μm.

Figure 5A:
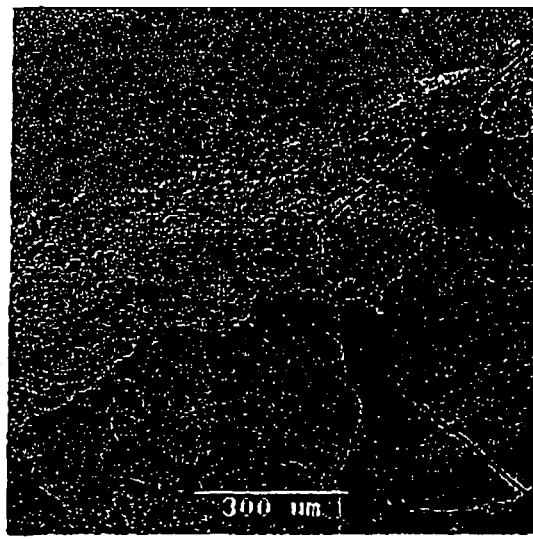
FIGS. 5a and 5b are electron microscope cross sectional views of a biocompatible implant with a micro-porous membrane.
Figure 5B:
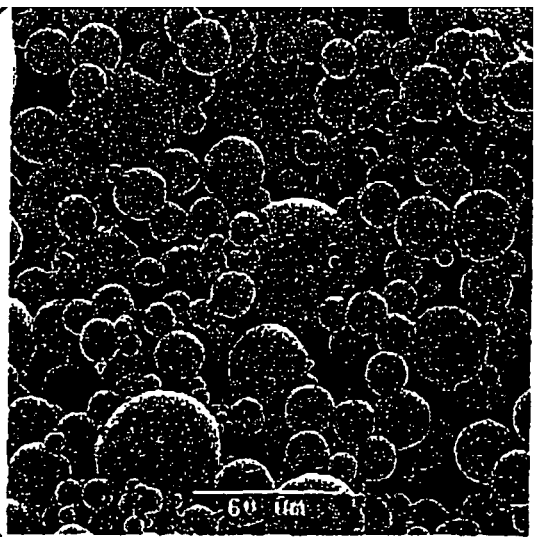

The scaffold or composite matrix is prepared by heat treatment as before in Examples 1-3. About 50 mg to 100 mg of the polymer microspheres are poured into the mold on the exposed surface of the scaffold or composite matrix. After about 1 min to about 3 min at 80° C. to 100° C. the polymer microspheres have linked with each other and with the surface of the scaffold or composite matrix. The mold is allowed to cool and the implant is removed out of the mold. With this process a biodegradable biocompatible implant is achieved having a barrier membrane sealed to its surface which is, in one embodiment, micro-porous. The pores in this embodiment have sizes within a range of about 5 min to about 30 μm. This is shown in the cross sectional views in FIGS. 5a and 5b. In FIG. 5a large granules form a part of the scaffold while the smaller microspheres are a part of the micro-porous barrier membrane.

The biocompatible implant according to the invention is a combination of a biocompatible scaffold or composite matrix which is shaped in accordance with the shape of the bone defect, and of a biocompatible barrier membrane which prohibits the in-growth of soft tissue and epithelial cells. The barrier membrane is interconnectively sealed to the exposed surface of the scaffold or composite matrix such that the biocompatible implant forms a single piece of matter. The barrier membrane on the finished biocompatible implant matches the form of the exposed surface of the scaffold or composite matrix. There is no need for an alignment of the membrane on the scaffold or composite matrix. There is no more surgery necessary to fix the barrier membrane or, subsequently, to remove the membrane. In some embodiments, both, the scaffold or composite matrix of the biodegradable biocompatible implant and the barrier membrane are advantageously biodegradable. Thus, they need not be removed from the healing site, but they are completely resorbed by the organism.

The biocompatible implant according to the invention is easy and cheap to manufacture. The preparation may be accomplished on site, e.g., by a physician or an assistant. While the invention has been described with reference to biocompatible implants for dental applications it will be appreciated by those skilled in the art that the biocompatible implants may also be used for the repair of bone defects of other skeleton parts. If, for example, a part of the skeleton is stricken by a tumor, the area stricken by the tumor may be removed and replaced by a biodegradable biocompatible implant according to the invention.

The invention claimed is:

1. Biocompatible implant for the treatment of defects in a living organism such as bone defects or tooth extraction wounds, comprising at least one zone of impermeability to soft tissue and/or epithelial cells in-growth, wherein said implant is comprised of an open porous scaffold and a membrane covering at least a part of said scaffold and being sealed to it such that said scaffold and said membrane form a single piece of matter that is resorbable by an organism, wherein at least a portion of the open porous scaffold allows an in-growth of regenerating bone tissue, wherein said scaffold is comprised of fused, biocompatible, biodegradable granules selected from the group consisting of solid granules, porous granules, hollow granules, hollow granules with at least one opening in the granule, and a mixture thereof; said granules having an equivalent-diameter in a range between about 100 µm to about 2000 µm, a major portion of said granules being coated with at least one biocompatible and biodegradable layer of a polymer selected from the group consisting of poly($\alpha$-hydroxyesters), poly(ortho esters), poly(ether esters), polyanhydrides, poly(phosphazenes), poly(propylene fumarates), poly(ester amides), poly(ethylene fumarates), poly (amino acids), polysaccharides, polypeptides, poly(hydroxy butyrates), poly(hydroxy valerates), polyurethanes, poly (malic acid), polylactides, polyglycolides, polycaprolactones, poly(glycolide-co-trimethylene carbonates), polydioxanones, and copolymers, terpolymers thereof, and blends thereof; and said polymer coating having a thickness in a range between 1 µm to 300 µm.

2. Biocompatible implant according to claim 1, wherein said implant is biodegradable.

3. Biocompatible implant according to claim 1, wherein said scaffold is comprised of a synthetic, biocompatible and biodegradable material.

4. Biocompatible implant according to claim 3, wherein said scaffold is comprised of a biopolymer, bioglass, bioceramic, calcium sulfate, or calcium phosphate.

5. Biocompatible implant according to claim 3, wherein said scaffold is comprised of monocalcium phosphate monohydrate, monocalcium phosphate anhydrous, dicalcium phosphate dihydrate, dicalcium phosphate anhydrous, tetracalcium phophate, calcium orthophosphate phosphate, calcium pyrophosphate, $\alpha$-tricalcium phosphate, $\beta$-tricalcium phosphate, or hydroxyapatite.

6. Biocompatible implant according to claim 3, wherein said scaffold is comprised of poly($\alpha$-hydroxyesters), poly (ortho esters), poly(ether esters), polyanhydrides, poly(phosphazenes), poly(propylene fumarates), poly(ester amides), poly(ethylene fumarates), poly(amino acids), polysaccharides, polypeptides, poly(hydroxy butyrates), poly(hydroxy valerates), polyurethanes, poly(malic acid), polylactides, polyglycolides, polycaprolactones, poly(glycolide-co-trimethylene carbonates), polydioxanones, or co-polymers, terpolymers thereof or blends thereof, or a combination of biocompatible and biodegradable materials.

7. Biocompatible implant according to claim 1, wherein said granules have an equivalent-diameter in a range between about 500 µm to about 1000 µm.

8. Biocompatible implant according to claim 1, wherein said polymer coating has a thickness in a range between 5 µm to 30 µm.

9. Biocompatible implant according to claim 1, wherein said granules have a spherical shape.

10. Biocompatible implant according to claim 1, wherein said scaffold has an open porous configuration with interconnected pores having a size in a range between about 10 µm to about 2000 µm.

11. Biocompatible implant according to claim 10, wherein said interconnected pores have a size in a range between about 100 µm to about 500 µm.

12. Biocompatible implant according to claim 1, wherein said membrane is made of a synthetic, biocompatible and biodegradable polymer selected from the group consisting of poly($\alpha$-hydroxyesters), poly(ortho esters), poly(ether esters), polyanhydrides, poly(phosphazenes), poly(propylene fumarates), poly(ester amides), poly(ethylene fumarates), poly (amino acids), polysaccharides, polypeptides, poly(hydroxy butyrates), poly(hydroxy valerates), polyurethanes, poly (malic acid), polylactides, polyglycolides, polycaprolactones, poly(glycolide-co-trimethylene carbonates), polydioxanones, and copolymers, terpolymers thereof, and blends thereof.

13. Biocompatible implant according to claim 1, wherein said biodegradable membrane is a polymer film, a polymer textile, a polymer fleece, a layer of fused polymer particles or a combination thereof, thus forming at least one zone of impermeability to soft tissue and/or epithelial cells in-growth, and having a thickness in a range between about 10 µm to about 3000 µm.

14. Biocompatible implant according to claim 1, wherein said biodegradable membrane is made of fused polymer particles.

15. Biocompatible implant according to claim 1, wherein said membrane has a configuration such as to allow a transport of fluids and/or molecules through the membrane, but forming a barrier against soft tissue and/or epithelial cells in-growth into the implant.

16. Biocompatible implant according to claim 1, wherein at least a portion of the membrane has a porous configuration, said porosity being formed by pores having sizes in the range between about 1 µm to 500 µm.

17. Biocompatible implant according to claim 16, wherein said pores have sizes in a range between about 5 µm to 50 µm.

18. Biocompatible implant according to claim 1, wherein said membrane comprises at least one non-porous layer.

19. Biocompatible implant according to claim 1, further comprising at least one biologically active substance which is integrated in said scaffold and/or in said granules and/or in a coating applied to the granules or implant and/or in said membrane and/or which is encapsulated in microspheres which are loaded into said scaffold and/or into said membrane and/or within macropores between said granules.

20. Biocompatible implant according to claim 1, further comprising at least one additive that is integrated into said scaffold and/or into said membrane.

21. Biocompatible implant according to claim 1, wherein an exposed surface of said biocompatible implant allows cell growth into the scaffold.

22. Biocompatible implant according to claim 1, wherein said biocompatible implant is seeded with cells.

23. Biocompatible implant for the treatment of defects in a living organism such as bone defects or tooth extraction wounds, comprising at least one zone of impermeability to soft tissue and/or epithelial cells in-growth, wherein said implant is comprised of an open porous scaffold and a membrane covering at least a part of said scaffold and being sealed to it such that said scaffold and said membrane form a single piece of matter that is resorbable by an organism, wherein at least a portion of the open porous scaffold allows an in-growth of regenerating bone tissue, wherein said biodegradable membrane is a polymer film, a polymer textile, a polymer fleece, a layer of fused polymer particles or a combination thereof, thus forming at least one zone of impermeability to soft tissue and/or epithelial cells in-growth, and having a thickness in a range between about 10 µm to about 3000 µm, wherein said at least one zone of impermeability to soft tissue and/or epithelial cells in-growth has a thickness in a range between about 50 µm to about 1000 µm.

24. Biocompatible implant for the treatment of defects in a living organism such as bone defects or tooth extraction wounds, comprising at least one zone of impermeability to soft tissue and/or epithelial cells in-growth, wherein said implant is comprised of an open porous scaffold and a membrane covering at least a part of said scaffold and being sealed to it such that said scaffold and said membrane form a single piece of matter that is resorbable by an organism, wherein at least a portion of the open porous scaffold allows an in-growth of regenerating bone tissue, wherein said biodegradable membrane is made of fused polymer particles, wherein said fused polymer particles comprise microspheres, pellets or granules, having a size smaller than about 500 µm.

25. Biocompatible implant for the treatment of defects in a living organism such as bone defects or tooth extraction wounds, comprising at least one zone of impermeability to soft tissue and/or epithelial cells in-growth, wherein said implant is comprised of an open porous scaffold and a membrane covering at least a part of said scaffold and being sealed to it such that said scaffold and said membrane form a single piece of matter that is resorbable by an organism, wherein at least a portion of the open porous scaffold allows an in-growth of regenerating bone tissue, wherein said membrane comprises at least two layers, one of said layers having a barrier function against soft tissue and/or epithelial cells in-growth in the scaffold, and a second layer, which is in direct contact with the surrounding living organism, allowing the stabilization and anchorage of soft tissue which tends to close the wound.

26. Biocompatible implant for the treatment of defects in a living organism such as bone defects or tooth extraction wounds, comprising at least one zone of impermeability to soft tissue and/or epithelial cells in-growth, wherein said implant is comprised of an open porous scaffold and a membrane covering at least a part of said scaffold and being sealed to it such that said scaffold and said membrane form a single piece of matter that is resorbable by an organism, wherein at least a portion of the open porous scaffold allows an in-growth of regenerating bone tissue, said scaffold and/or said membrane including void spaces that are at least partially filled with at least one of air or gas, polymer, liquid, gel, or solid particles.

27. Biocompatible implant for the treatment of defects in a living organism such as bone defects or tooth extraction wounds, comprising at least one zone of impermeability to soft tissue and/or epithelial cells in-growth, wherein said implant is comprised of an open porous scaffold and a membrane covering at least a part of said scaffold and being sealed to it such that said scaffold and said membrane form a single piece of matter that is resorbable by an organism, wherein at least a portion of the open porous scaffold allows an in-growth of regenerating bone tissue, further comprising at least one additive that is integrated into said scaffold and/or into said membrane, wherein said at least one additive comprises a plasticizer.

28. Biocompatible implant for the treatment of defects in a living organism such as bone defects or tooth extraction wounds, comprising at least one zone of impermeability to soft tissue and/or epithelial cells in-growth, wherein said implant is made of a composite matrix and a membrane covering at least a part of said composite matrix and being sealed to it such that said composite matrix and said membrane form a single piece of matter, said composite matrix comprising a plurality of inorganic or synthetic granules bonded or held together by a synthetic polymer matrix, said inorganic or synthetic granules selected from the group consisting of solid granules, porous granules, hollow granules, hollow granules with at least one opening in the granule, and a mixture thereof; said granules having an equivalent-diameter in a range between about 100 µm to about 2000 µm.

29. Biocompatible implant according to claim 28, wherein said implant is biodegradable.

30. Biocompatible implant according to claim 28, said inorganic or synthetic granules comprising at least one of biopolymers, bioglasses, bioceramics, or a polymer selected from the group consisting of poly($\alpha$-hydroxyesters), poly (ortho esters), poly(ether esters), polyanhydrides, poly(phosphazenes), poly(propylene fumarates), poly(ester amides), poly(ethylene fumarates), poly(amino acids), polysaccharides, polypeptides, poly(hydroxy butyrates), poly(hydroxy valerates), polyurethanes, poly(malic acid), polylactides, polyglycolides, polycaprolactones, poly(glycolide-co-trimethylene carbonates), polydioxanones, and co-polymers, terpolymers thereof and blends thereof, or a combination of biocompatible and biodegradable materials.

31. Biocompatible implant according to claim 30, wherein said inorganic or synthetic granules comprise calcium sulfate or calcium phosphate.

32. Biocompatible implant according to claim 31, wherein said inorganic or synthetic granules comprise monocalcium phosphate monohydrate, monocalcium phosphate anhydrous, dicalcium phosphate dihydrate, dicalcium phosphate anhydrous, tetracalcium phophate, calcium orthophosphate phosphate, calcium pyrophosphate, $\alpha$-tricalcium phosphate, $\beta$-tricalcium phosphate, or apatite.

33. Biocompatible implant according to claim 32, wherein said inorganic or synthetic granules comprise hydroxyapatite.

34. Biocompatible implant according to claim 28, said synthetic polymer matrix comprising at least one of poly($\alpha$-hydroxyesters), poly(ortho esters), poly(ether esters), polyanhydrides, poly(phosphazenes), poly(propylene fumarates), poly(ester amides), poly(ethylene fumarates), poly(amino acids), polysaccharides, polypeptides, poly(hydroxy butyrates), poly(hydroxy valerates), polyurethanes, poly (malic acid), polylactides, polyglycolides, polycaprolactones, poly(glycolide-co-trimethylene carbonates), polydioxanones, and copolymers, terpolymers thereof, and blends thereof.

35. Biocompatible implant according to claim 28, said composite matrix having an open porous configuration with interconnected pores having a size in a range between about 10 µm to about 2000 µm.

36. Biocompatible implant for the treatment of defects in a living organism such as bone defects or tooth extraction wounds, comprising at least one zone of impermeability to soft tissue and/or epithelial cells in-growth, wherein said implant is made of a composite matrix and a membrane covering at least a part of said composite matrix and being sealed to it such that said composite matrix and said membrane form a single piece of matter, said composite matrix comprising a plurality of inorganic or synthetic granules bonded or held together by a synthetic polymer matrix, said composite matrix including void spaces between adjacent granules that are at least partially filled with at least one of air or gas, polymer, liquid, gel, or solid particles.

37. Biocompatible implant for the treatment of defects in a living organism such as bone defects or tooth extraction wounds, comprising at least one zone of impermeability to soft tissue and/or epithelial cells in-growth, wherein said implant is made of a composite matrix and a membrane covering at least a part of said composite matrix and being sealed to it such that said composite matrix and said membrane form a single piece of matter, said composite matrix comprising a plurality of inorganic or synthetic granules bonded or held together by a synthetic polymer matrix, said composite matrix including void spaces between adjacent granules that are filled with at least a biologically active substance.

38. Biocompatible implant for the treatment of defects in a living organism such as bone defects or tooth extraction wounds, comprising at least one zone of impermeability to soft tissue and/or epithelial cells in-growth, wherein said implant is made of a composite matrix and a membrane covering at least a part of said composite matrix and being sealed to it such that said composite matrix and said membrane form a single piece of matter, said composite matrix comprising a plurality of inorganic or synthetic granules bonded or held together by a synthetic polymer matrix, wherein said biodegradable membrane is a polymer film, a polymer textile, a polymer fleece, a layer of fused polymer particles or a combination thereof, thus forming at least one zone of impermeability to soft tissue and/or epithelial cells in-growth, and having a thickness of about 10 μm to about 3000 μm.

\* \* \* \* \*